(12) United States Patent
Ko et al.

(10) Patent No.: US 12,019,082 B2
(45) Date of Patent: Jun. 25, 2024

(54) APPARATUS FOR MEASURING GLYCATION OF RED BLOOD CELLS AND GLYCATED HEMOGLOBIN LEVEL USING PHYSICAL AND ELECTRICAL CHARACTERISTICS OF CELLS, AND RELATED METHODS

(71) Applicant: ORANGE BIOMED LTD., CO., Seoul (KR)

(72) Inventors: Ung Hyeon Ko, Seoul (KR); Seung Jin Kang, Seoul (KR); Eun Young Park, Seoul (KR)

(73) Assignee: ORANGE BIOMED LTD., CO., Seoul (KR)

(*) Notice: Subject to any disclaimer, the term of this patent is extended or adjusted under 35 U.S.C. 154(b) by 0 days.

(21) Appl. No.: 18/364,436

(22) Filed: Aug. 2, 2023

(65) Prior Publication Data
US 2024/0019448 A1    Jan. 18, 2024

Related U.S. Application Data

(60) Division of application No. 18/064,233, filed on Dec. 9, 2022, now Pat. No. 11,747,348, which is a
(Continued)

(30) Foreign Application Priority Data

Sep. 29, 2021  (KR) .................. 10-2021-0128520

(51) Int. Cl.
*G01N 33/72* (2006.01)
*B01L 3/00* (2006.01)
(Continued)

(52) U.S. Cl.
CPC ...... *G01N 33/726* (2013.01); *B01L 3/502715* (2013.01); *G01N 33/49* (2013.01);
(Continued)

(58) Field of Classification Search
CPC .... G01N 33/726; G01N 33/49; G01N 33/723; G01N 33/80; B01L 3/502715;
(Continued)

(56) References Cited

U.S. PATENT DOCUMENTS 5,206,144 A   4/1993 Zeuthen et al.
5,642,734 A   7/1997 Ruben et al.
(Continued)

FOREIGN PATENT DOCUMENTS

EP    1162449 A1   12/2001
EP    2182345 B1    6/2013
(Continued)

OTHER PUBLICATIONS

International Search Report dated Jul. 11, 2022 for International Patent Application No. PCT/KR2021/018280, 3 pages.
(Continued)

*Primary Examiner* — Brian J. Sines
(74) *Attorney, Agent, or Firm* — Perkins Coie LLP

(57) ABSTRACT

The present disclosure relates to systems and methods for measuring glycated A1c hemoglobin. A glycated hemoglobin level measuring system includes a sample testing apparatus having a microchannel that compresses a blood sample traveling through, a first pair of electrodes coupled to the microchannel, and a second pair of electrodes coupled to the microchannel. The glycated hemoglobin level measuring system further includes an analysis apparatus having sensors coupled to the first and second pairs of electrodes and configured to calculate a travel time taken by a red blood cell to pass through the first and second pairs of electrodes. The glycated hemoglobin level measuring system can use the travel time to measure a rigidity of the red blood cells and the corresponding glycated hemoglobin level.

10 Claims, 9 Drawing Sheets

Related U.S. Application Data continuation-in-part of application No. PCT/KR2021/018280, filed on Dec. 3, 2021.

(51) Int. Cl.
  *G01N 33/49* (2006.01)
  *G01N 33/80* (2006.01)

(52) U.S. Cl.
  CPC ........... *G01N 33/723* (2013.01); *G01N 33/80* (2013.01); *B01L 2200/027* (2013.01); *B01L 2200/10* (2013.01); *B01L 2200/14* (2013.01); *B01L 2300/0645* (2013.01); *B01L 2300/0816* (2013.01); *B01L 2300/087* (2013.01); *B01L 2400/0403* (2013.01)

(58) Field of Classification Search
  CPC ........... B01L 2200/027; B01L 2200/10; B01L 2200/14; B01L 2300/0645; B01L 2300/0816; B01L 2300/087; B01L 2400/0403
  See application file for complete search history.

(56) References Cited

U.S. PATENT DOCUMENTS

| | | |
|---|---|---|
| 6,204,668 B1 | 3/2001 | Sequeira et al. |
| 6,399,293 B1 | 6/2002 | Pachl et al. |
| 6,949,070 B2 | 9/2005 | Ishler |
| 8,252,163 B2 | 8/2012 | Sugiyama et al. |
| 8,789,405 B2 | 7/2014 | Sugiyama |
| 9,017,536 B2 | 4/2015 | Oishi et al. |
| 9,080,939 B2 | 7/2015 | Tsai et al. |
| 9,429,579 B2 | 8/2016 | Sugiyama et al. |
| 9,795,328 B2 | 10/2017 | Taub et al. |
| 9,977,037 B2 | 5/2018 | Yoshida et al. |
| 10,641,724 B2 | 5/2020 | Ainger et al. |
| 10,996,187 B2 | 5/2021 | Lee et al. |
| 11,009,479 B2 | 5/2021 | Liu et al. |
| 11,111,517 B2 | 9/2021 | Ichiyanagi et al. |
| 11,376,590 B2 | 7/2022 | Gurkan et al. |
| 11,385,244 B2 | 7/2022 | Shigemitsu et al. |
| 11,400,452 B2 | 8/2022 | Jagtiani |
| 11,747,348 B2 * | 9/2023 | Ko .................. G01N 33/80 436/67 |
| 2010/0089774 A1 | 4/2010 | Manohar et al. |
| 2010/0145174 A1 | 6/2010 | Alferness et al. |
| 2010/0178660 A1 | 7/2010 | Adamczyk et al. |
| 2015/0268244 A1 | 9/2015 | Cho et al. |
| 2018/0235524 A1 | 8/2018 | Dunn et al. |
| 2018/0364186 A1 | 12/2018 | Watkins et al. |
| 2019/0232287 A1 | 8/2019 | Depa et al. |
| 2020/0101456 A1 | 4/2020 | Watkins et al. |
| 2020/0200734 A1 | 6/2020 | Yu et al. |
| 2021/0025904 A1 | 1/2021 | Snodgrass et al. |
| 2021/0072137 A1 | 3/2021 | Michel et al. |
| 2021/0229102 A1 | 7/2021 | Jagtiani |
| 2021/0239717 A1 | 8/2021 | Clarke et al. |
| 2021/0293693 A1 | 9/2021 | Bharadwaj et al. |
| 2022/0065876 A1 | 3/2022 | Connolly |
| 2022/0134339 A1 | 5/2022 | Hayashino et al. |
| 2022/0187184 A1 | 6/2022 | Al et al. |
| 2022/0362779 A1 | 11/2022 | Jagtiani |

FOREIGN PATENT DOCUMENTS

| | | |
|---|---|---|
| EP | 2568281 B1 | 11/2018 |
| EP | 2144057 B1 | 4/2019 |
| EP | 2995947 B1 | 1/2020 |
| JP | 2002538459 A | 11/2002 |
| JP | 2012529033 A | 11/2012 |
| JP | 2017521679 A | 8/2017 |
| KR | 20050120637 A | 12/2005 |
| KR | 20070061042 A | 6/2007 |
| KR | 10-2012-0111878 A | 10/2012 |
| KR | 10-2015-0126476 A | 10/2012 |
| KR | 10-2013-0066841 A | 6/2013 |
| KR | 10-2015-0108050 A | 9/2015 |
| KR | 20150108050 A | 9/2015 |
| KR | 101584083 B1 | 1/2016 |
| KR | 101666847 B1 | 10/2016 |
| KR | 101681170 B1 | 12/2016 |
| KR | 101802289 B1 | 12/2017 |
| KR | 101818368 B1 | 1/2018 |
| KR | 101884314 B1 | 8/2018 |
| KR | 101885964 B1 | 8/2018 |
| KR | 101995253 B1 | 7/2019 |
| KR | 102104654 B1 | 4/2020 |
| KR | 20200097068 A | 8/2020 |
| KR | 102174557 B1 | 11/2020 |
| KR | 102281500 B1 | 7/2021 |
| KR | 102315843 B1 | 10/2021 |
| KR | 102403577 B1 | 5/2022 |
| KR | 102439240 B1 | 9/2022 |
| WO | 2010137470 A1 | 12/2010 |
| WO | 2013153406 A1 | 10/2013 |

OTHER PUBLICATIONS

Tsai, et al., "Impedance measurement system for automatic determination of glycated hemoglobin", Rev. Sci. Instrum. 89, 065003, https://doi.org/10.1063/1.5025151, Jun. 28, 2018, 10 pages.

* cited by examiner

APPARATUS FOR MEASURING GLYCATION OF RED BLOOD CELLS AND GLYCATED HEMOGLOBIN LEVEL USING PHYSICAL AND ELECTRICAL CHARACTERISTICS OF CELLS, AND RELATED METHODS

CROSS-REFERENCE TO RELATED APPLICATIONS

This application is a division of U.S. patent application Ser. No. 18/064,233, filed Dec. 9, 2022, which is a continuation-in-part of International Application PCT/KR2021/018280, filed Dec. 3, 2021, which claims the benefit of Korean Patent Application No. 10-2021-0128520, filed Sep. 29, 2021, issued as Korean Patent No. 10-2439474, each of which are hereby incorporated by reference for all purposes in its entirety.

TECHNICAL FIELD

This present disclosure relates to measuring one or more characteristics associated with glycated A1c hemoglobin.

BACKGROUND

A blood sugar test, which is generally performed to diagnose diabetes, measures the level of glucose in the blood and yields a blood sugar level. However, the blood sugar level is a temporary value and may change before or after meals, or according to other factors.

By contrast, a glycated hemoglobin test measures the level of glucose linked or combined within the hemoglobin residing in red blood cells. While the red blood cells are in blood, they are able to bind with glucose within the blood. By measuring or estimating an average amount of glucose that has been attached to hemoglobin over time, the glycated hemoglobin test can measure the glucose level accumulated over the average lifespan of a red blood cell (e.g., three months). Therefore, the glycated hemoglobin test is less affected by physical activities or food intake than other blood sugar tests. That is, the glycated hemoglobin level is more stable than the blood sugar level and may be a better reference for diagnosing diabetes.

However, conventional glycated hemoglobin level measuring devices require complex technology and equipment that have limited accessibilities (e.g., only accessible to hospitals and laboratory levels of institutions). While continuous management of glycated hemoglobin level is required to manage diabetes and its prognosis, patients have very few options for tracking such management. Moreover, efforts to develop such accessible management methods are only recently being developed. Like blood sugar measurement devices that have been popularized for home use, efforts are being made to enable measurement of glycated hemoglobin level at home without visiting a clinic (see, e.g., Korean Patent Registration Publication KR2281500 (registration date: Jul. 20, 2021)). However, such efforts focus on biochemical methods that have several disadvantages, including lifespan limitations for required components, difficult storage methods, and low or unreliable measurement accuracy attributable to poor storage conditions or the skills of the user.

BRIEF DESCRIPTION OF THE DRAWINGS

Features, aspects, and advantages of the presently disclosed technology may be better understood with regard to the following drawings.

Figure 1:
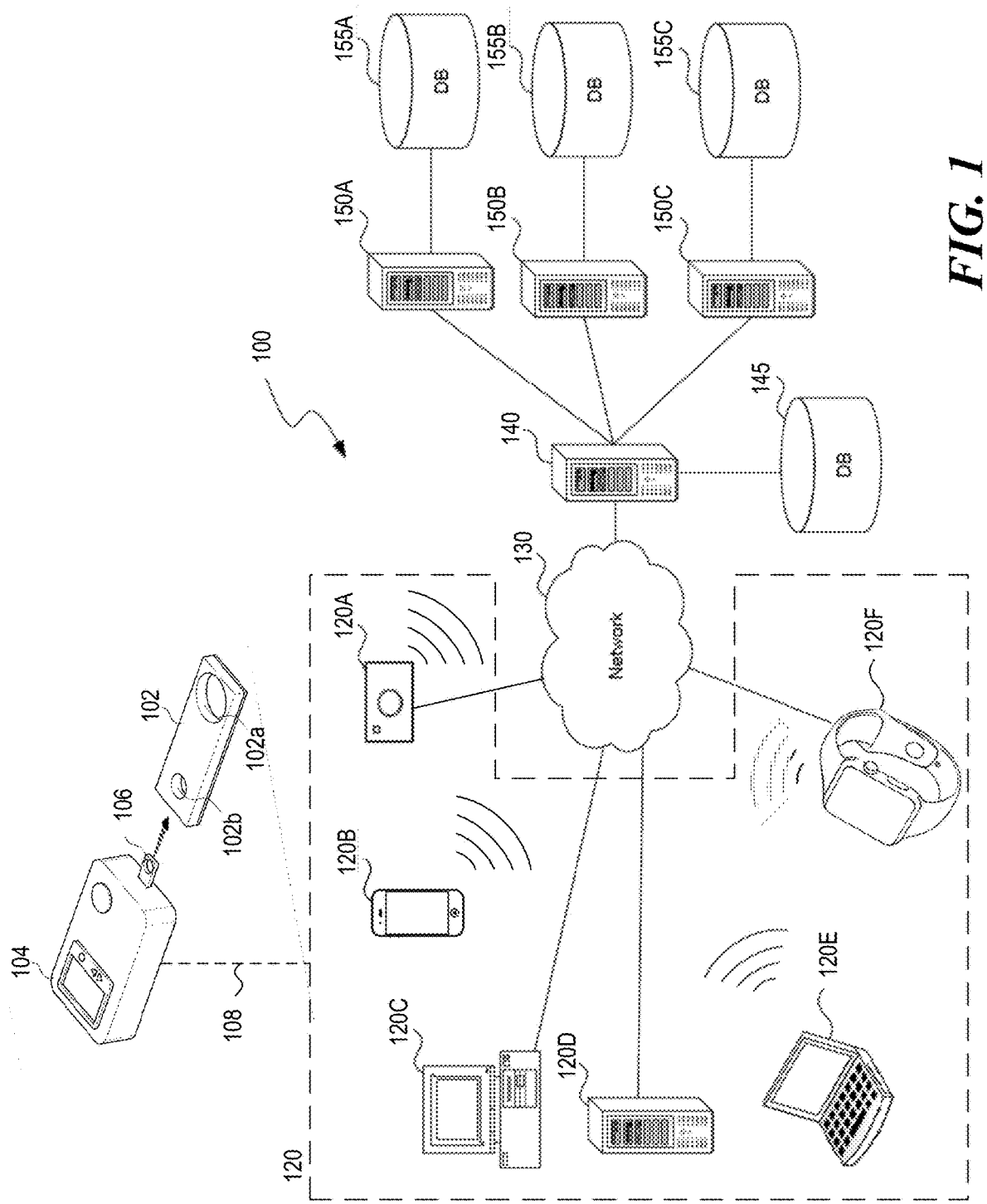
FIG. 1 is a block diagram illustrating an environment in which some embodiments of a glycated hemoglobin level measuring system can operate.

A person skilled in the relevant art will understand that the features shown in the drawings are for purposes of illustrations, and variations, including different and/or additional features and arrangements thereof, are possible.

DETAILED DESCRIPTION

The following disclosure describes systems, devices, and methods for measuring analyte levels. More specifically, the present technology relates to a device that leverages microchannel manufacturing technology to measure an analyte level, such as glycated hemoglobin level, at home. More specifically, one or more embodiments of the present technology include measuring a glycated hemoglobin level based on one or more physical characteristics of a sample. For example, the glycated hemoglobin level can be determined based on measured change(s) in one or more physical characteristics (e.g., mechanical characteristics, deformability, stiffness, etc.) of a glycated red blood cell.

In some embodiments, a glycated hemoglobin level measuring system includes an analysis apparatus couplable to a sample testing apparatus that includes an inlet, an outlet, and a microchannel connected between the inlet and the outlet. The sample testing apparatus can be configured to test or observe one or more characteristics of particulates suspended in fluid. As an illustrative example, the sample testing apparatus can be configured to test or observe a stiffness or a rigidity of red blood cells suspended within blood samples. The inlet can be configured to receive the blood sample, and the outlet can be configured to collect the blood sample exiting the microchannel. To facilitate the test, the microchannel can have one or more dimensions less than that/those of the red blood cells, thereby compressing the red blood cells that travel through the microchannel from the inlet to the outlet. The sample testing apparatus can further include at least a first set (e.g., at least one pairing) and a second set (e.g., at least one pairing) of electrodes configured to facilitate detection of the red blood cells within the microchannel. The first set of electrodes can be closer to (e.g., within a threshold distance from) the inlet. The second set of electrodes can be closer to the outlet and spaced apart from the first set of electrodes by a predetermined distance. The first and second sets of electrodes can respectfully surround and define at least a first detection region and a second detection region.

The analysis apparatus can include a pump couplable to an inlet, an outlet, or both and can be configured to facilitate a transfer of fluid with particulates (e.g., red blood cells) suspended therein through the microchannel from the inlet to the outlet. The analysis apparatus can further include an electrical source that is (1) couplable to the first and second sets of electrodes and (2) configured to communicate a first signal through the first set of electrodes and a second signal through the second pair of electrodes. The glycated hemoglobin level measuring system can be configured (via, e.g., electrolytes within the microchannel) to allow the first and second signals respectfully traverse across the first and second detection regions and through the corresponding first and second pairs of electrodes. The communicated first and second signals can correspond to one or more reference characteristics, such as one or more initial impedances across the first and second detection regions, initial phases of the first and second signal, or the like. The analysis apparatus can include a first sensor couplable to the first pair of electrodes and configured to measure a change in an electrical property (e.g., an impedance across the first detection region, a phase shift, or the like) caused by a particulate reaching and passing through the first detection region. Similarly, the analysis apparatus can include a second sensor couplable to the second pair of electrodes and configured to measure a change in an electrical property caused by a particulate reaching and passing through the second detection region.

The analysis apparatus further includes a logic configured to detect a first time based on the change in impedance for the first signal and a second time based on the change in impedance for the second signal. In other words, the logic can detect the first and second times as representations of the moment when the particulate reaches the respective first and second detection regions. The logic can calculate a time difference between the first and second times, such that the time difference represents a travel period between the first and second detection regions. Since the particulates are compressed while moving across the microchannel, its rigidity can affect the travel period. Accordingly, the logic can use one or more predetermined relationships (via, e.g., corresponding equations, lookup tables, or the like) to determine the stiffness of the particulate (e.g., a corresponding glycated hemoglobin level for the red blood cells) based on the time difference. The glycated hemoglobin level can include levels of HbA1a, HbA1b, and/or HbA1c.

In some embodiments, an analyte measuring system includes an analysis apparatus configured to measure one or more analytes in a sample. The sample can be a biological fluid, such as blood, interstitial fluid, or the like. The analytes can include, for example, glycosylated hemoglobin, hemoglobin variants, hemoglobin A, hemoglobin S, hemoglobin C, hemoglobin D, hemoglobin E, hemoglobin F, and/or substance or chemical constituent in a biological fluid from a host (e.g., a human). The analysis apparatus can determine analyte levels one based one or more characteristics of constituents or components (e.g., cells) in the sample. The characteristics can be determined based on movement of cells along a cell-deforming passageway. The cells can be held in a compressed state while traveling along the detection zone of the cell-deforming passageway. For example, a column of spaced apart compressed cells can travel one at a time through the detection zone. The analyte measuring system can determine the analyte level based on a speed of the cells, resident time of the cell in a cell-deforming passageway, or the like. The concentration of cells in the sample can be decreased (e.g., by adding a solution to the sample) or increased to increase or decrease, respectively, the average spacing between adjacent cells. For example, the spacing can be increased to reduce the occurrence of overlapping cells in the detection zone. The number and configuration of cell-deforming passageways can be selected based on the number of analyses to be performed.

In some embodiments, an analyte measuring system can include an impedance detector with at least one cell-deforming passageway and a controller programmed to detect individual cells in the cell-deforming passageway, determine at least one movement parameter for the individual cells in the cell-deforming microchannel or passageway, and determine an analyte level based on the determined at least one movement parameter. The movement parameter can be a speed (e.g., speed of the cell), a duration or period of time (e.g., a period of time to travel a predetermined distance along the cell-deforming channel or passageway), acceleration/deceleration profiles (e.g., deceleration profile of cells in the downstream direction along the), combinations thereof, or the like. The impedance detector can measure impedance (e.g., at a single location or multiple locations) along the cell-deforming passageway(s) to identify over lapping cells, cells close to one another (e.g., two or more cells within a detection zone of the cell-deforming channel through which energy pass or a field is located), cells (e.g., red blood cells, white blood cells, platelets, etc.) touching one another, and/or cells (e.g., white blood cells) to be disregarded from the analysis. For example, the analyte measuring system can process signals from the impedance detector to identify multi-cell impedance signals indicating over lapping cells or cells to close to one another (e.g., physically touching one another) and/or abnormal-impedance signals indicating abnormal cells (e.g., abnormal cells associated with diseases, such as anemias, including sickle cell anemia), or the like. The cell-deforming passageway can have a unfirm or varying cross section along its length.

The impedance detector can be part of a disposable or reusable sampling device electrically couplable to an analysis apparatus. The analysis apparatus can be a handheld device with a display, the controller, and power source. The controller can be programmed to execute one or more programs for determining analyte information based on one or more characteristics of cells in biological samples, the movement parameter, or the like.

For illustrative purposes, the present technology is described with respect to measuring one or more aspects related to glycation of red blood cells. However, it is understood that the present technology can be used to measure or analyze other fluid-suspended particulates and/or characteristics thereof.

Operating Environment

FIG. 1 is a block diagram illustrating an environment in which some embodiments of a glycated hemoglobin level measuring system can operate. The glycated hemoglobin level measuring system can include a sample testing apparatus 102 and an analysis apparatus 104 couplable to the sample testing apparatus 102 via a connector 106. The sample testing apparatus 102 can include an inlet 102a configured to receive a blood sample, and an outlet 102b configured to release the blood sample. The inlet 102a may be larger in width and/or depth than the outlet 102b for easier entry of the blood sample.

The analysis apparatus 104 can communicate, via a direct wired or wireless communication link 108 or a network 130, with one or more client computing devices 120, examples of which include an imaging device 120A, a smart phone or tablet 120B, a desktop computer 120C, a computer system 120D, a laptop computer 120E, and a wearable device 120F. These are only examples of some of the devices, and other embodiments can include other computing devices, such as other types of personal and/or mobile computing devices. Client computing devices 120 can collect various data from a user (e.g., analyte data from a wearable analyte monitor (for example, a continuous glucose monitor (CGM)), sleep data, heart rate data, blood pressure data, dietary information, exercise data, health metrics, etc.) and communicate the collected data to the analysis apparatus 104 and/or a service provider (e.g., a remote device/system, such as a server). The collected data can be leveraged for the testing/measuring processes. For example, the analysis apparatus 104 can include a processing system programmed to provide output based on correlates between real-time CGM data and glycated A1c hemoglobin levels. For example, the processing system can include controller with one or more processors, memory storing programs analyzing the collected data executable to, for example, identify individual cells, overlapping cells, speed of travel of cells, flow rate of samples, etc. The client computing devices 120 can also communicate information, such as test results or other notifications, from the analysis apparatus 104 and/or the service provider to the user.

Accordingly, the computer devices 120 can operate in a networked environment using logical connections through network 130 to the analysis apparatus 104 and/or one or more remote computers, such as a server computing device or a cloud computing environment. The networked environment can also be used to provide software updates to algorithms used in the analysis apparatus 104 and/or the one or more client computing devices 120. In some embodiments, the server 140 can be an edge server which receives client requests and coordinates fulfillment of those requests through other servers, such as servers 150A-C. Server computing devices 140 and 150 can include computing systems. Though each server computing device 140 and 150 is displayed logically as a single server, server computing devices can each be a distributed computing environment encompassing multiple computing devices located at the same or at geographically disparate physical locations. In some implementations, each server 150 corresponds to a group of servers.

Client computing devices 120 and server computing devices 140 and 150 can each act as a server or client to other server/client devices. Server 140 can connect to a database 145. For example, the servers 150A-C can each connect to a corresponding database 155A-C. As discussed above, each server 150 can correspond to a group of servers, and each of these servers can share a database or can have their own database. Databases 145 and 155 can warehouse (e.g., store) information. Though databases 145 and 155 are displayed logically as single units, databases 145 and 155 can each be a distributed computing environment encompassing multiple computing devices, can be located within their corresponding server, or can be located at the same or at geographically disparate physical locations.

Network 130 can be a local area network (LAN), a wide area network (WAN), and/or other wired, wireless, or combinational networks. Portions of network 130 may be the Internet or some other public or private network. Client computing devices 120 can be connected to network 130 through a network interface, such as by wired or wireless communication. While the connections between server 140 and servers 150 are shown as separate connections, these connections can be any kind of local, wide area, wired, or wireless network, including network 130 or a separate public or private network.

In some embodiments, the analysis apparatus 104 can initiate one or more tests for the blood sample collected at the testing apparatus 102. The analysis apparatus 104 can interact with the testing apparatus 102 to collect and analyze one or more measurements regarding the blood sample. The analysis apparatus 104 can communicate the analysis results to the server 140 corresponding to other entities, such as a healthcare provider, a further health tracking or comprehensive health analysis service, or the like. Alternatively, the analysis apparatus 104 can provide the measurements to the server 140 (e.g., without local analysis at the analysis apparatus 104), and the remote service provider can analyze the provided measurements.

Testing Configuration

Figure 2:
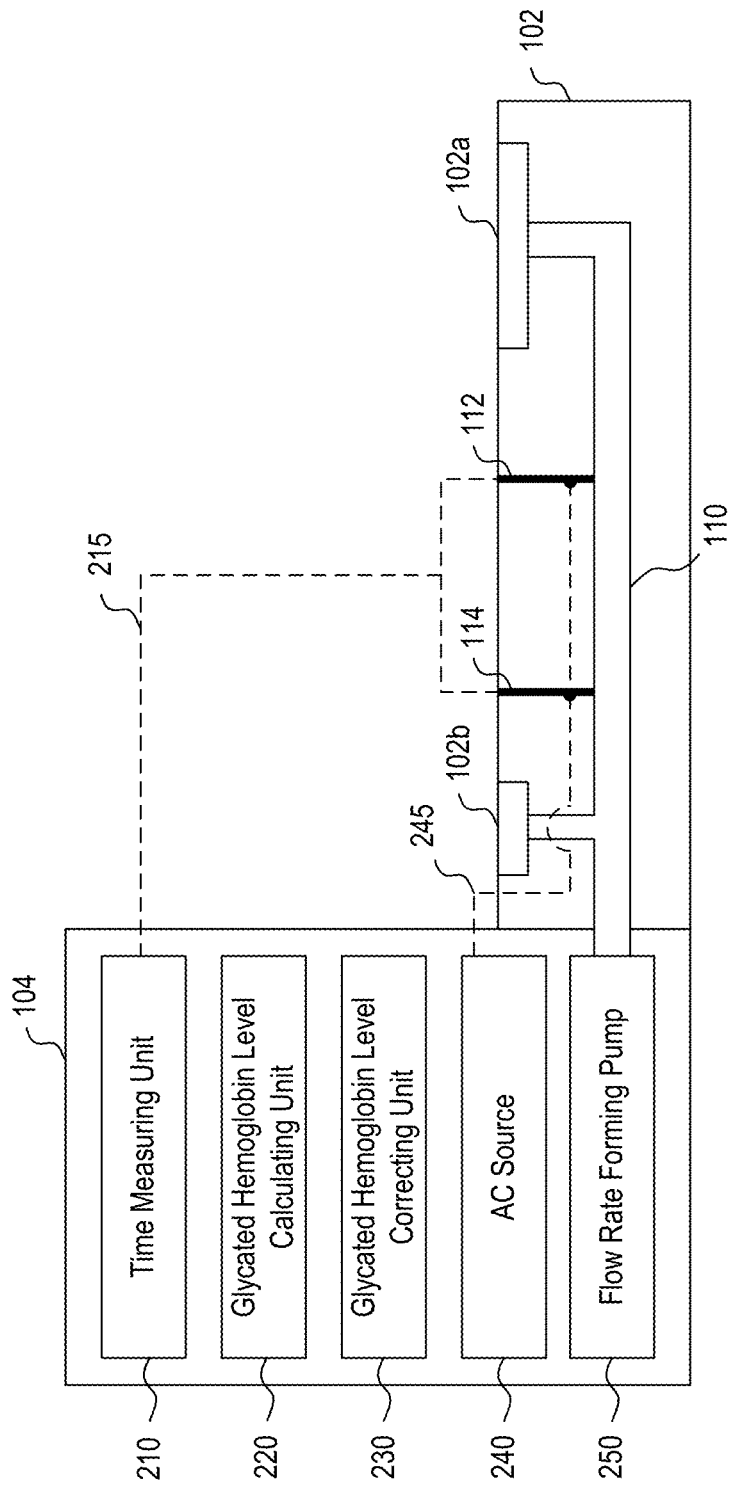
FIG. 2 is a block diagram illustrating an analysis apparatus and a sample testing apparatus of the glycated hemoglobin level measuring system according to some embodiments of the present technology.
Figure 3:
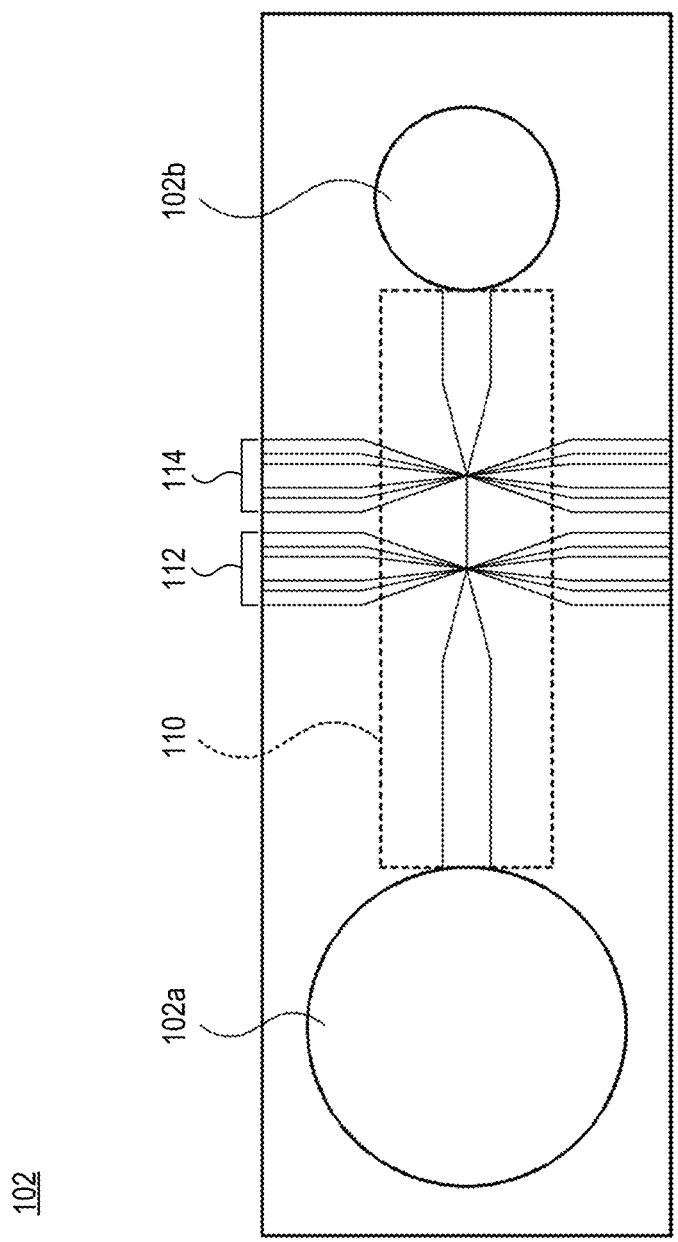
FIG. 3 is a cross-sectional view of the sample testing apparatus according to some embodiments of the present technology.
Figure 4:
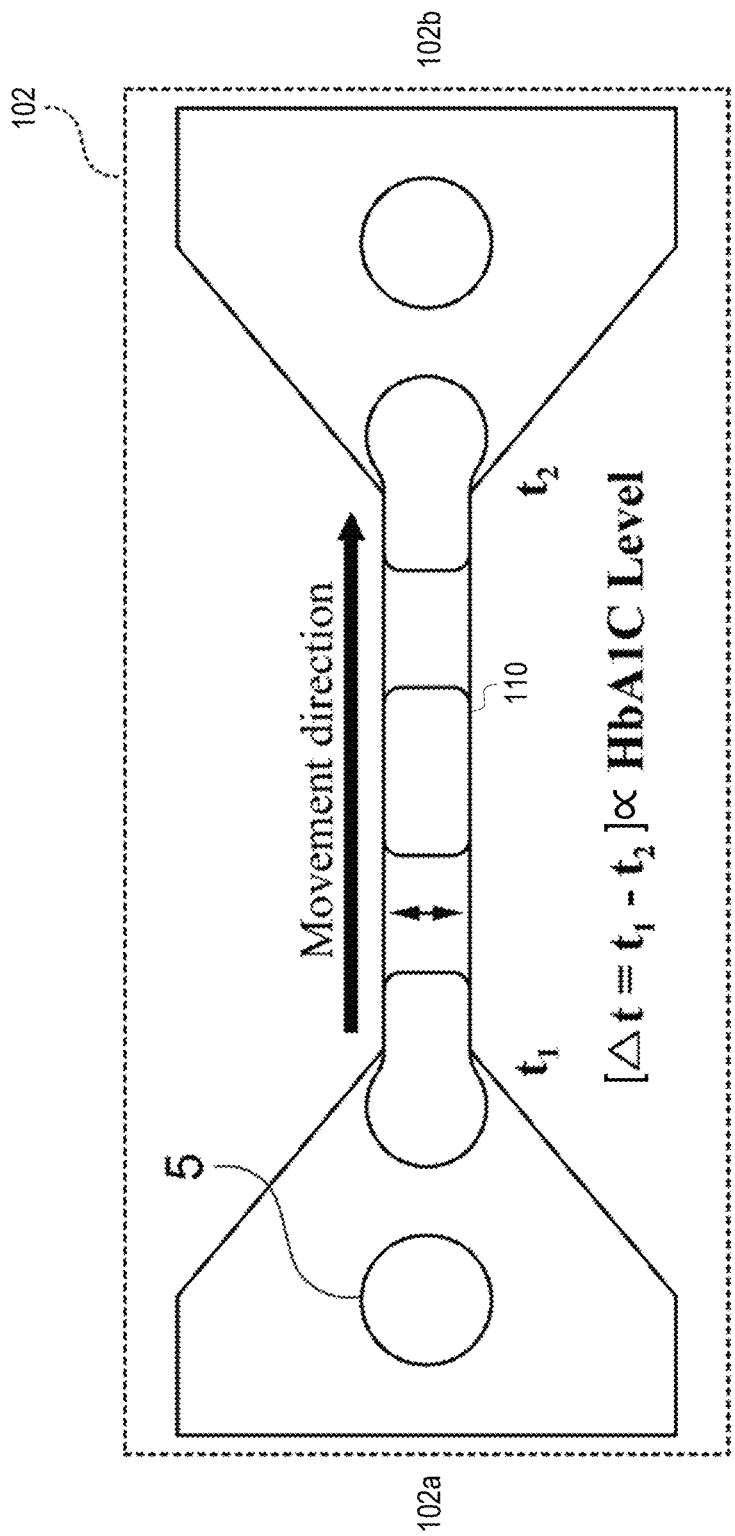
FIG. 4 is a cross-sectional view of the sample testing apparatus with a red blood cell inside according to some embodiments of the present technology.

FIGS. 2-5 illustrate various aspects of an example testing configuration. FIG. 2 is a block diagram illustrating the analysis apparatus 104 and the sample testing apparatus 102 of the glycated hemoglobin level measuring system according to some embodiments of the present technology. FIG. 3 is a cross-sectional view of the sample testing apparatus 102 according to some embodiments of the present technology. FIG. 4 is a cross-sectional view of the microchannel 110 showing movement of a red blood cell 5 inside according to some embodiments of the present technology.

Referring to FIGS. 2-5 together, the sample testing apparatus 102 can include a plate-shaped chip. The microchannel 110 can be disposed on a substrate and connected between the inlet 102a and the outlet 102b, which are externally exposed. The microchannel 110 can be configured to transfer the blood sample from the inlet 102a to the outlet 102b.

The microchannel 110 can alter the configuration of red blood cells (e.g., by compressing or deforming the red blood cells) to affect movement of the red blood cells along the microchannel 110 due to, for example, interaction between surfaces of the microchannel 110 and the red blood cell. For example, frictional forces between surfaces of the microchannel 110 and the red blood cell can be proportional to the outward pressure applied by compressed red blood cells to the walls of the microchannel 110. The microchannel 110 can be configured to allow sliding of the compressed red blood cells along the microchannel 110. The frictional forces are greater for stiffer red blood cells associated with higher A1c hemoglobin levels, thereby causing those stiffer red blood cells to travel at a lower speed than highly compliant blood cells associated with lower A1c hemoglobin levels. This results in movement of the red blood cells along microchannel 110 indicating A1c hemoglobin levels. The configuration of the microchannel 110 can be selected based on the characteristic(s) of the cells to be analyzed and detection techniques (e.g., impedance detection techniques, optical detection techniques, etc.).

In some embodiments, the microchannel 110 can have a width that is less than the average, uncompressed dimension of the average diameter of a red blood cell. The microchannel 110 can have a height that is greater than an average thickness of the red blood cell by a threshold value or range. Alternatively, the microchannel 110 can have a height that is less than the average, uncompressed thickness of the targeted particulate by a threshold value or range. Accordingly, the microchannel 110 can be configured to allow one red blood cell to enter and travel through at any given cross-section. Based on the at least one undersized dimension, the microchannel 110 can compress the traversing red blood cells. For example, the average human red blood cell can have a diameter about 7 to 8 micrometers and a thickness about 2-3 micrometers. Accordingly, the width of the microchannel 110 can range between 4 and 10 micrometers, and the height of the microchannel 110 can range between 1 and 5 micrometers. Dimensions can be selected based on based on shape (e.g., rectangular, square, elliptical, etc.) of the cross-section of the microchannel 110.

The microchannel 110 can have the undersized dimension for measuring a stiffness or a rigidity of the red blood cells suspended in the blood sample. When the hemoglobin in a red blood cell binds with glucose and become glycated, the elasticity of the red blood cell can decrease, causing the red blood cell to harden. Therefore, a red blood cell with a glycated hemoglobin can travel slower and take a longer duration to pass through a portion or entire length of the microchannel 110 than a red blood cell with a non-glycated hemoglobin. The analysis apparatus 104 can measure and/or analyze the duration of the red blood cells passing through a detection zone or entire the microchannel 110 for measuring the glycation level of the red blood cells.

To facilitate the duration measurements, the sample testing apparatus 102 can have a first set of electrodes 112 and a second set of electrodes 114 on or embedded in the substrate and extending generally perpendicular to the microchannel 110. The first set of electrodes 112 can be located closer to the inlet 102a (e.g., within a threshold distance from the inlet 102a) than the outlet 102b. The second set of electrodes 114 can be located between the first set of electrodes 112 and the outlet 102b and closer to the outlet 102b (e.g., within a threshold distance from the outlet 102b). The first and second sets of electrodes 112 and 114 may be separated by a predetermined distance along the microchannel 110 that ranges between 300 and 800 micrometers.

In some embodiments, the inlet 102a and/or the microchannel 110 can include an electrolyte (e.g., mixed with the blood sample) configured to facilitate the movement of the red blood cells and allow an electric current to flow between the electrodes. In the illustrated embodiment (FIG. 3), each of the first and second sets of electrodes 112 and 114 have three electrodes (e.g., two adjacent pairings of electrodes). In other embodiments, each of the first and second sets of electrodes 112 and 114 may have two, three, or more electrodes. Additional electrodes may be used to increase the measurements of the travel time, the cell size, and/or the cell type. The number of electrodes may be the same or differ between the first and second sets of electrodes 112 and 114.

The first set of electrodes 112 can be separated by one or more predetermined intervals along the microchannel. Accordingly, the first set of electrodes 112 can define at least a first detection region on the microchannel 110 and between the electrodes. Similarly, the second set of electrodes 114 can be separated by one or more predetermined intervals along the microchannel 110, thereby defining a second detection region on the microchannel 110 and between the electrodes. The separation length between each pairing of electrodes of the first and/or second detection regions may be based on an average and/or estimated length of the blood cell. In some embodiments, the separation length can range between 5 and 25 micrometers.

The length of each electrode may range between 5 and 25 micrometers. The width of each of the electrodes may increase at portions distant from the microchannel 110. In other words, the electrodes can limit the narrow width to portions closest to the microchannel, such as to facilitate the measurements, and have wider portions elsewhere to increase connection strength to other electrical components and to reduce heat generated by the signals passing through the electrodes.

The analysis apparatus 104 can include an electrical source (e.g., AC source) 240 coupled to the first and second sets of electrodes 112 and 114. The electrical source 240 can be configured to communicate one or more input signals 245 (e.g., an oscillating signal having a magnitude of 2V or less) through the first and second sets of electrodes 112 and 114 (e.g., in parallel). In some embodiments, the sample testing apparatus 102 can be configured (via, e.g., electrolyte within the microchannel 110) to communicate the one or more input signals 245 as a sinusoidal wave across the first and second detection regions and through the corresponding pairs of electrodes. The configuration can establish one or more electrical characteristics, such as initial impedances, initial phases, or the like, for the signals communicated across the first and second detection regions. The electrodes 112 and 114 may be configured to electrically couple and/or directly contact the blood sample passing through the microchannel 110. Accordingly, the blood cell reaching or passing through the first and second detection regions can alter the one or more electrical characteristics. In other words, the current flowing between the electrodes may change when the red blood cell 5 reaches the first or second detection regions between the electrodes.

The analysis apparatus 104 also has various circuitry (e.g., logic), including a time measuring unit 210 configured to receive one or more return signals 215 from the first and second sets of electrodes 112 and 114. The time measuring unit 210 can detect a first time $t_1$ based on a change in impedance as represented by changes in the return signal 215 from the first set of electrodes 112 (e.g., a result of the input signal 245 traversing through the first detection region and across a red blood cell). The first time $t_1$ can represent the moment a red blood cell reaches the first detection region. Similarly, time measuring unit 210 can detect a second time $t_2$ based on a change in impedance as represented by changes in the return signal from the second set of electrodes 114 (e.g., a result of the second signal 245 traversing through the second detection region and across the red blood cell) and representing the moment the red blood cell reaches the second detection region. The time measuring unit 210 can calculate a time difference $\Delta t$ between the first and second times. The time difference $\Delta t$ corresponds to a travel time of the red blood cell across a predetermined distance between the first and second sets of electrodes. As described above, the travel time can correspond to the rigidity of the red blood cell.

Various algorithms can be used to remove noise in the data, such as thermal noise spikes and/or overlapped red blood cells. For example, the time measuring unit 210 can track pairings of first and second times corresponding to each red blood cell. Accordingly, the time measuring unit 210 can ensure that the time difference $\Delta t$ is within a predetermined range (e.g., a range within 0.01-10 millimeters per second) that corresponds to expected or reasonable movement speeds of the red blood cells. When the time difference Δt is outside of the predetermined range, the time measuring unit 210 can remove the corresponding first time and the second time. In removing both the first and second times, the time measuring unit 210 can eliminate the corrupted data.

The analysis apparatus 104 can also include a glycated hemoglobin level calculating unit 220 configured to determine a glycated hemoglobin level based on the time difference. For example, the glycated hemoglobin level calculating unit 220 can use a predetermined relationship or pattern (e.g., an equation, a lookup table, or the like) between various travel times and corresponding red blood cell rigidity levels and/or glycated hemoglobin levels. The glycated hemoglobin level calculating unit 220 can use the calculated time difference Δt as an input into the predetermined relationship to determine the corresponding glycated hemoglobin level for the traversed red blood cell.

The analysis apparatus 104 can further include a glycated hemoglobin level correcting unit 230 configured to personalize the determined glycated hemoglobin level. For example, the glycated hemoglobin level correcting unit 230 can adjust the determined glycated hemoglobin level according to a reference glycated hemoglobin level of the user. The reference glycated hemoglobin level can include a previously determined hemoglobin level, such as an initially measured level before implementation of one or more disease management mechanisms or a level measured under one or more targeted conditions (e.g., clinical conditions). Alternatively or additionally, the reference glycated hemoglobin level can correspond to one or more determined or verified characteristics of the patient's red blood cell (e.g., rigidity associated with patient's age, sex, or other contributing factors). The glycated hemoglobin level correcting unit 230 can utilize a predetermined method, process, or the like to adjust the determined glycated hemoglobin level according to the reference glycated hemoglobin level.

The analysis apparatus 104 can further include a pump 250 couplable to the inlet 102a, the outlet 102b, and/or the microchannel 110. The pump 250 can be configured to provide pressure and/or vacuum to the sample testing apparatus 102 to facilitate transfer of the blood sample and the red blood cells through the microchannel 110 from the inlet 102a to the outlet 102b. The pump 250 can be configured to provide a predetermined level or range of force to push the red blood cells through the microchannel 110. Once the red blood cell enters, the microchannel 110 can be configured to facilitate the movement via capillary action.

For multi-analyte detection, the correcting unit 230 can be configured detect other analyte levels. Multi-analyte sample testing apparatuses can include multiple microchannels configured to provide different alterations to samples. For example, the correcting unit 230 can adjust operation to detect additional analyte levels according to reference levels of the user. Those reference levels can include a previously determined level for those analytes of interest. Alternatively or additionally, the reference levels can correspond to one or more determined or verified characteristics of the patient's sample correlated or uncorrelated with glycated hemoglobin levels.

Example Measurements and Analysis

Figure 5:
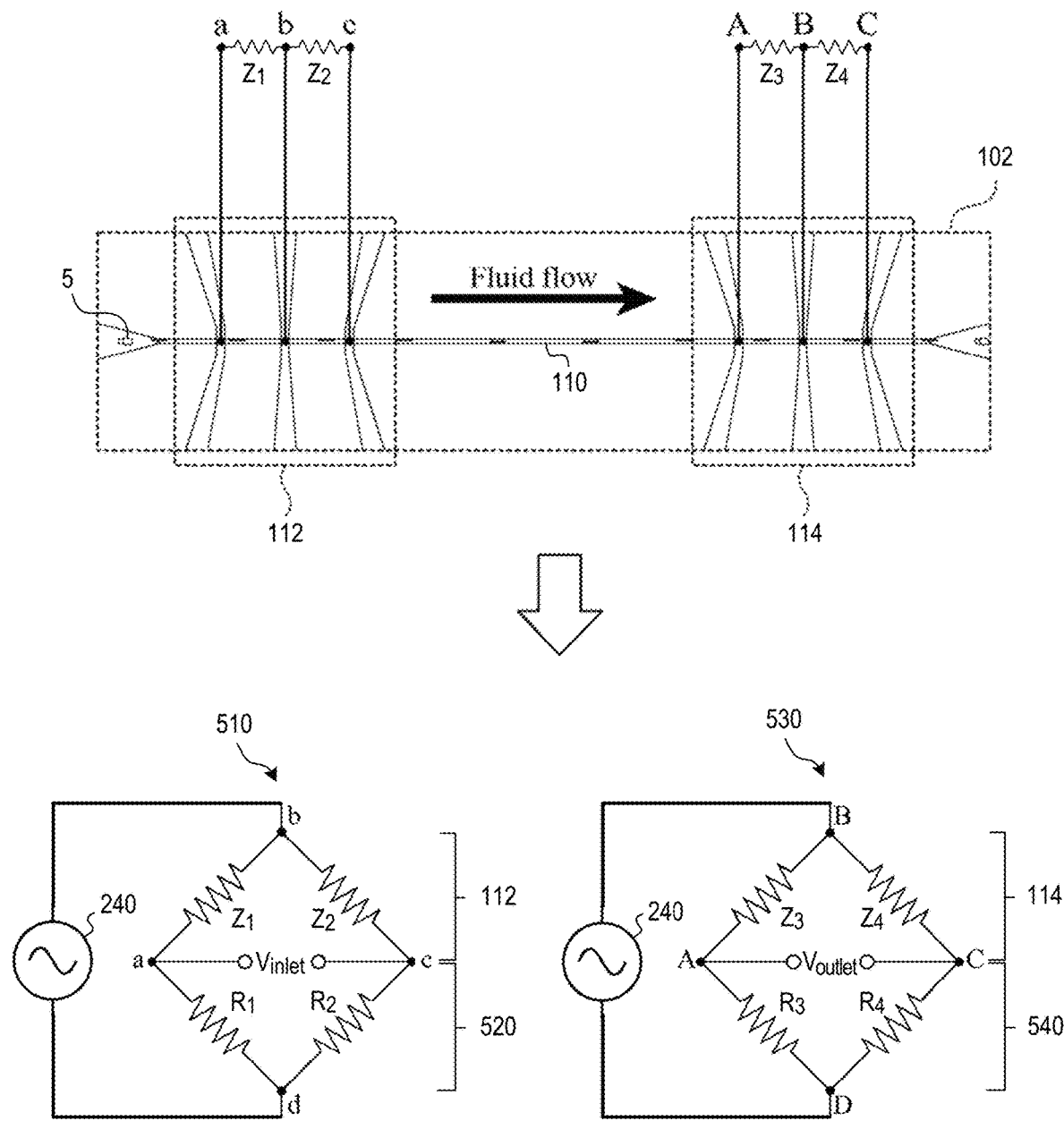
FIG. 5 is a schematic illustrating an operation of the glycated hemoglobin level measuring system according to some embodiments of the present technology.

FIG. 5 is a schematic illustrating an operation of the glycated hemoglobin level measuring system according to some embodiments of the present technology. In some embodiments, the first set of electrodes 112 can include three electrodes (e.g., two adjacent and overlapping pairings of electrodes) connected to nodes a, b, and c located at the microchannel 110. The AC source 240 can send the input signal 245 of FIG. 2 to node b. The input signal 245 can traverse to nodes a and b, such as via electrolyte in a reference state. Given the signal path between nodes a and b and nodes b and c, the path between nodes a and b can have a first impedance $Z_1$, and the path between nodes b and c can have a second impedance $Z_2$.

Similarly, in some embodiments, the second set of electrodes 114 can include three electrodes connected to nodes A, B, and C located at the microchannel 110. The AC source 240 can send the input signal 245 to node B. The signal path between nodes A and B can have a third impedance $Z_3$, and the path between nodes B and C can have a fourth impedance $Z_4$. The red blood cell 5 can change the impedance between the nodes when the red blood cell 5 reaches the detection region between the corresponding electrodes. As the red blood cell 5 travels through the microchannel 110 along a fluid flow direction, the red blood cell 5 can sequentially affect impedances $Z_1$, $Z_2$, $Z_3$, and then $Z_4$.

The input signal 245 to nodes b and B can have an amplitude less than 2V (e.g., between 100 mV to 1.4 V). The input signal 245 can have a low current value (e.g., on the order of microamps). The alternating current can have a targeted frequency that ranges between 1 kHz to 100 kHz. If the frequency of the input signal is below a floor threshold, it can induce unwanted electrolysis in the microchannel 110 due to the ions within the electrolyte. If the frequency is above a ceiling threshold, the input signal may consume excessive or ineffective amount of energy and may generate overwhelming or unrecoverable noise levels.

The analysis apparatus 104 includes first and second sensors 520 and 540 couplable to the first and second sets of electrodes 112 and 114. In some embodiments, the time measuring unit 210 can include the first and second sensors 520 and 540. When coupled, the sensors 520 and 540 can be configured to measure changes in the impedance values $Z_1$ through $Z_4$. In the illustrated embodiment, the first sensor 520 and the coupled first set of electrodes 112 can form a Wheatstone bridge circuit. Using the Wheatstone bridge formation, the sensors 520 can increase the measurement accuracy and detect relatively small changes in impedance values and/or other signal characteristics. The first component (left side) of the first sensor 520 can have a first resistor with a predetermined resistance $R_1$ connected in series with the path between nodes a and b and the corresponding first impedance $Z_1$. The second component (right side) of the first sensor 520 can have a second resistor with a predetermined resistance $R_2$ connected in series with the path between nodes b and c and the corresponding second impedance $Z_2$.

Similarly, the first component (left side) of the second sensor 540 can have a third resistor with a predetermined resistance $R_3$ connected in series with the path between nodes A and B and the corresponding third impedance $Z_3$. The second component (right side) of the second sensor 540 can have a fourth resistor with a predetermined resistance $R_4$ connected in series with the path between nodes B and C and the corresponding third impedance $Z_4$. Each of the first and second sensors 520 and 540 can complete the circuit path for the alternating current (AC) source 240.

In some embodiments, the electrodes for nodes a, b, and c (and A, B, and C) can have a separation distance according to an average dimension of the red blood cell 5. For example, the separation distance can be configured to have one red blood cell between adjacent pair of the nodes, and the separation distance between nodes a and b and the separation distance between nodes b and c can be equal. Accordingly, impedances between adjacent pairings of the nodes can be equal and the signals detected at nodes a and b can match and at nodes A and B can match before the red blood cell reaches the detection regions. The above-described Wheatstone bridge circuits can be balanced to an equilibrium state as represented by the equations:

$$Z_1 \times R_2 = Z_2 \times R_1, \text{ and}$$

$$Z_3 \times R_4 = Z_4 \times R_3.$$

The red blood cell can alter the impedance between nodes a and b and the signal detected at node a when the red blood cell reaches the corresponding detection region. Afterwards, once the red blood cell passes through to the detection region between nodes b and c, the impedance between nodes a and b and the signal detected at node a can return to reference levels. Also, the red blood cell can alter the impedance between nodes b and c and the signal detected at node c. In other words, the red blood cell can cause an imbalance in the Wheatstone bridge circuit and cause a difference in the signals traveling through the left and right sides of the Wheatstone bridge circuit.

From the first set of electrodes 112, the analysis apparatus 104 can read the difference in signals across nodes a and b or at $V_{inlet}$. The analysis apparatus 104 can detect the first time $t_1$ when the difference between nodes a and b has a non-zero magnitude. From the second set of electrodes 114, the analysis apparatus 104 can read the difference in signals across nodes A and B or at $V_{outlet}$.

The analysis apparatus 104 (via, e.g., the glycated hemoglobin level calculating unit 220) can determine a size and/or a type of the passing cell based on one or more details regarding the change in impedance values. The determined size and type can be used to improve the accuracy of the determined glycated hemoglobin level.

Figure 6A:
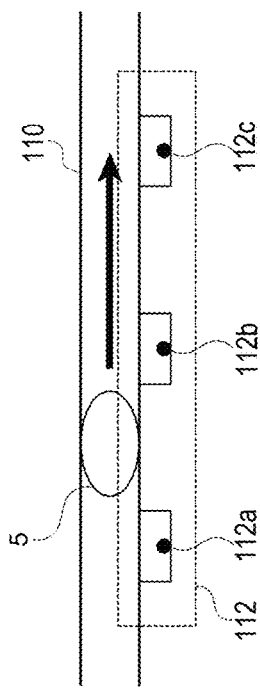
FIGS. 6A and 6B are diagrams illustrating a red blood cell at different locations inside of a microchannel of the sample testing apparatus according to some embodiments of the present technology.
Figure 6B:
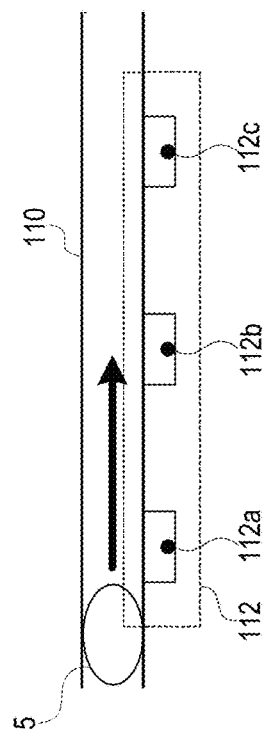
Figure 7A:
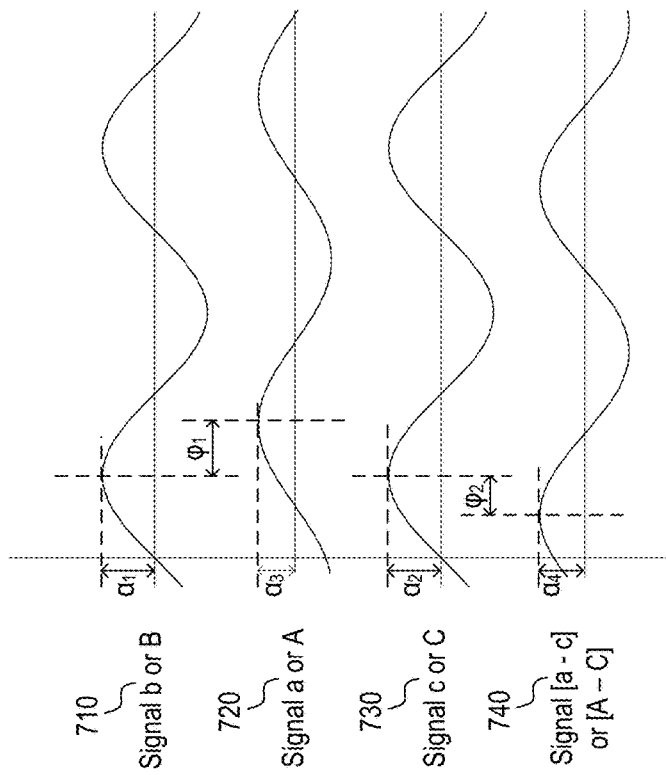
FIGS. 7A and 7B are diagrams illustrating various signals corresponding to FIGS. 6A and 6B according to some embodiments of the present technology.
Figure 7B:
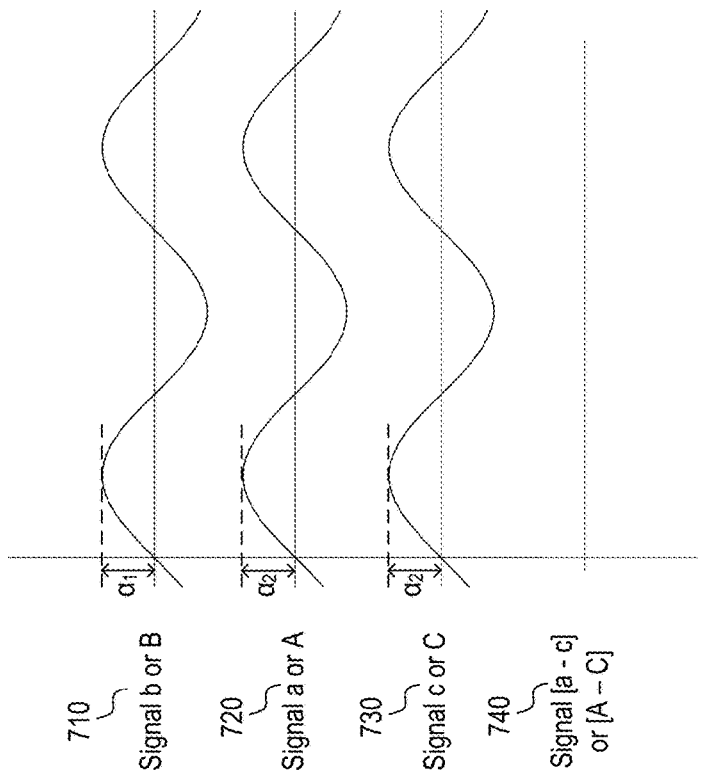

FIGS. 6A and 6B are diagrams illustrating a red blood cell 5 at different locations inside of the microchannel 110 of the sample testing apparatus 102 according to some embodiments of the present technology. FIGS. 7A and 7B are diagrams illustrating various signals corresponding to FIGS. 6A and 6B according to some embodiments of the present technology. The signal (e.g., alternating current) 710 sent to node 112b can have an amplitude $\alpha_1$.

In FIG. 6A, the red blood cell 5 has not yet reached the detection regions of the microchannel 110 between the nodes 112a, 112b, and 112c. Therefore, the impedances between the nodes 112a and 112b and between nodes 112b and 112c can match each other.

FIG. 7A can illustrate the input and detected signals for the state illustrated in FIG. 6A. In FIG. 7A, the signals 720 and 730 detected at nodes 112a and 112c can match each other and have no signal difference 740 between signals a and c.

When the red blood cell 5 reaches a detection region between nodes 112a and 112b (FIG. 6B), the signal detected at node a may be impacted by the presence of the red blood cell 5 (FIG. 7B). Therefore, the signal 720 can an amplitude $\alpha_3$ that is less than the amplitude $\alpha_1$ of the input signal 710 and/or $\alpha_2$. The signal 720 can also experience a phase shift $\varphi_1$ relative to the input signal 710. The signal 730 across node 112c can remain in the reference state with amplitude $\alpha_2$ and without experiencing any phase shift since there is no red blood cell between nodes 112b and 112c. Accordingly, the signal difference 740 between signals a and c can have a non-zero amplitude $\alpha_4$ and a phase shift $\varphi_2$ relative to the input signal 710. The signals and their amplitudes and phase shifts illustrated in FIGS. 7A and 7B are not to scale, and can be different in other embodiments.

In the case of an error condition in the microchannel 110 (e.g., two red blood cells that entered the microchannel at different times simultaneously passing the detection region), the first set of electrodes 112 may detect two separate red blood cells, but the second set of electrodes 114 may detect only one red blood cell due to the error condition. In this case, the next reading by the second set of electrodes 114 (e.g., a third red blood cell) may be recognized as not corresponding to the second reading by the first set of electrodes 112 (e.g., the second red blood cell), and be considered abnormal given the average speed of a red blood cell traveling through the microchannel (0.2 to 6.0 mm/sec). The glycated hemoglobin level measuring system may consequently omit those abnormal signal readings instead of pairing the wrong inlet and outlet cells. This abnormality detection may also be based on a predetermined average time period necessary for a red blood cell to travel from the first to the second set of electrodes 112 and 114. The glycated hemoglobin level measurement system can use additional sensors near or at the inlet 102a and the outlet 102b to measure an overall test time, which can be used to normalize all collected data. This also facilitates comparison of collected data points.

Figure 8A:
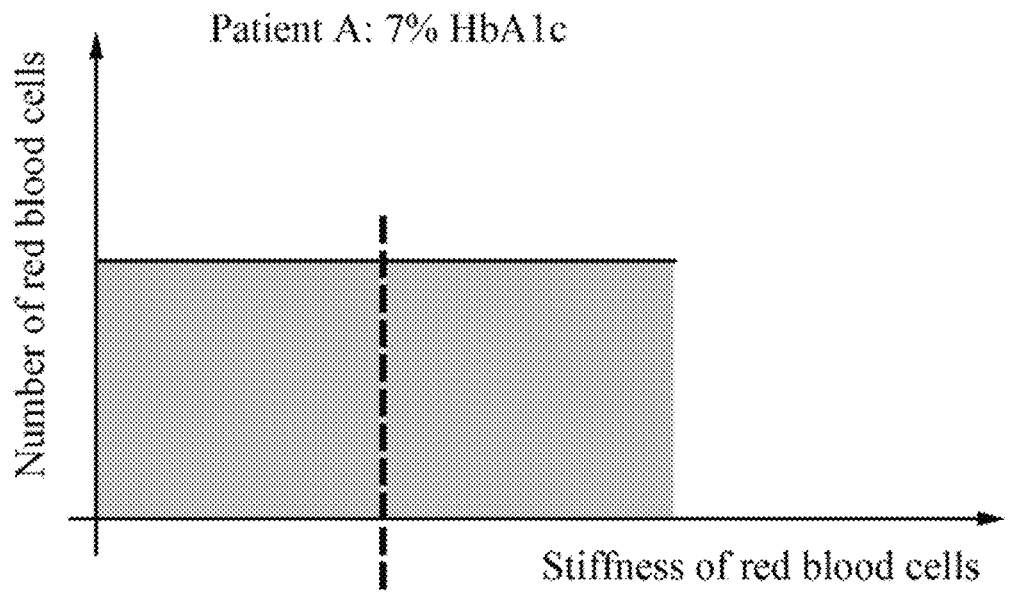
FIGS. 8A and 8B are diagrams illustrating distributions of the determined stiffness of red blood cells representative of different management statuses according to some embodiments of the present technology.
Figure 8B:
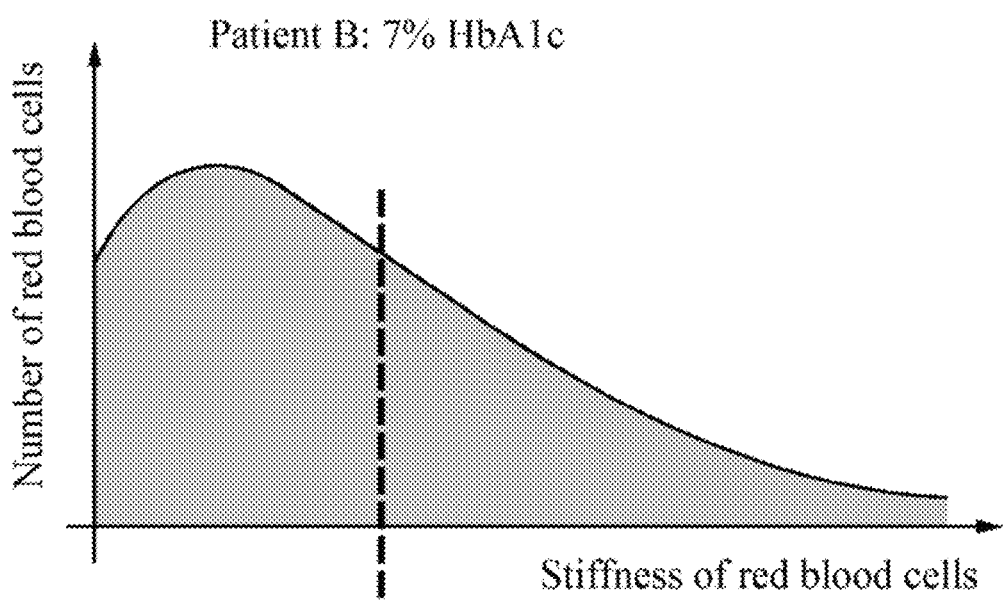

FIGS. 8A and 8B are diagrams illustrating distributions of the determined stiffness of red blood cells of different management statuses according to some embodiments of the present technology. For example, FIGS. 8A and 8B can represent patients having the same average glycated hemoglobin level (e.g., 7% HbA1c) but different treatment statuses, such as before and after implementing a management mechanism (e.g., a new drug).

A given blood sample can include several hundred red blood cells or more with varying degrees of stiffness, such as according to different ages of the red blood cells. The glycated hemoglobin level measuring system can use the distribution of the stiffness measurements to determine a management status of the user's glycated hemoglobin level. The average life span of the red blood cells present in the blood sample can have a determinable effect on the glycated hemoglobin level. When a patient's diabetes or glycated hemoglobin level is not properly managed, or when the management remains unchanged over a period of time, the proportion of red blood cells having a particular glycated hemoglobin level may be generally consistent for different red blood cells with different ages. However, when a patient starts managing or adjusts the management of their glycated hemoglobin level, the glycated hemoglobin level in newly made red blood cells can decrease. Accordingly, the number of red blood cells with relatively low stiffness can increase. These changes may appear as features of the corresponding distribution.

FIG. 8A can illustrate the stiffness distribution of a first patient who is not managing their glucose level, and FIG. 8B can illustrate the stiffness distribution of a second patient who is managing their glucose level. The first patient can have a more uniform stiffness distribution. On the other hand, the second patient have a more varied stiffness distribution because older red blood cells may be glycated while younger red blood cells are not due to the second patient beginning to manage their glucose level. That is, the uniformity of the stiffness level of the red blood cells decreases. Therefore, the glycated hemoglobin level measuring system can objectively determine the health management status of the user by tracking any changes in the distribution of the calculated glycated hemoglobin level data. Accordingly, the glycated hemoglobin level measuring system can enable healthcare professionals to provide better prescriptions and to improve management of chronic diseases by providing direct feedback on a patient's implemented management strategies using the stiffness distribution, as well as on the current status based on a representative value of the glycated hemoglobin level. In addition, the feedback data can allow healthcare professionals to assess and compare the effectiveness of particular adjustments or prescriptions to other options and those of other patients, thereby allowing healthcare professionals to personalize the management plan for each individual patient.

Additionally, the response profiles can be crowd-sourced and paired with other physiological and/or demographic markers. The service provider can analyze such paired data, such as using machine learning or artificial intelligence mechanisms, and determine patterns in effectiveness of specific treatment options according to the different markers. The service provider can further leverage the learned patterns to optimize and personalize the treatment plans for each patient according to their physiological and/or demographic traits.

Control Flow

Figure 9:
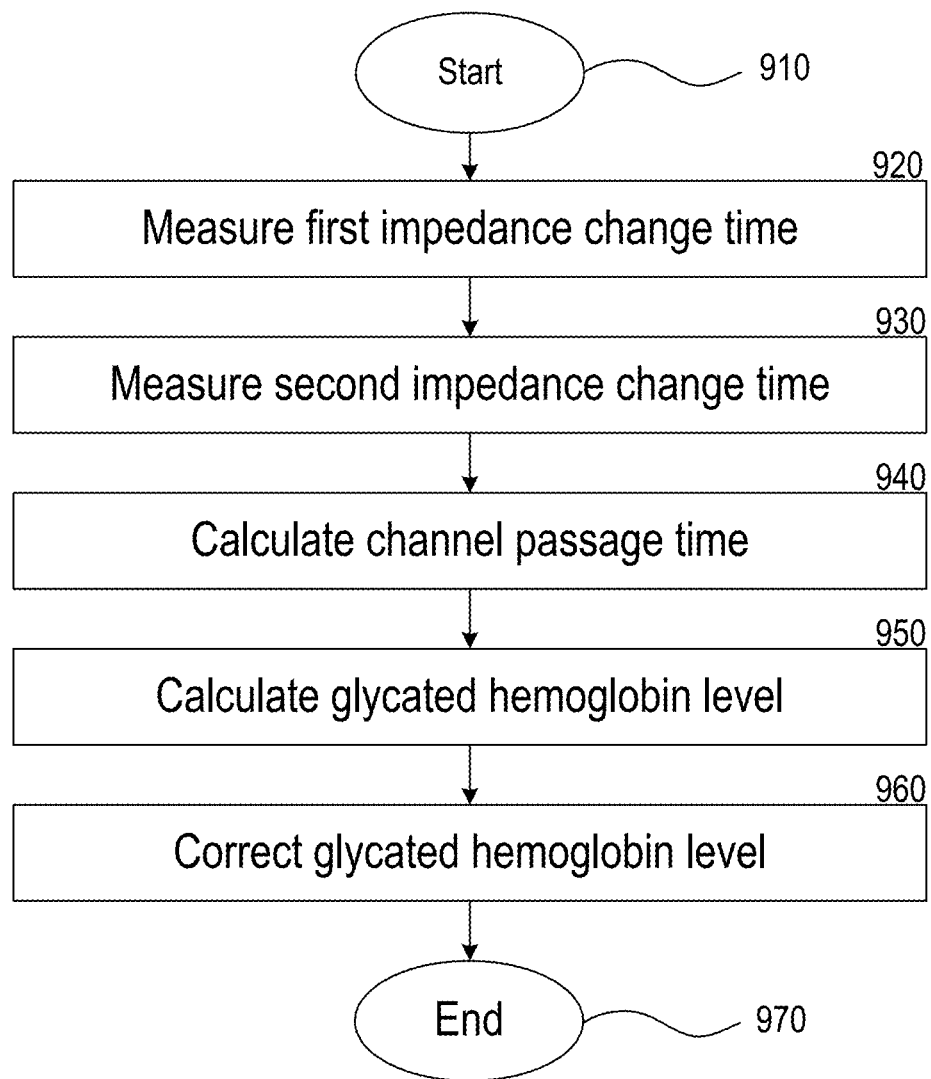
FIG. 9 is a flow diagram illustrating a method of operating the glycated hemoglobin level measuring system according to some embodiments of the present technology.

FIG. 9 is a flow diagram illustrating a method 900 of operating the glycated hemoglobin level measuring system according to some embodiments of the present technology. At the start 910, the glycated hemoglobin level measuring system can receive a blood sample provided by the user. At block 920, the glycated hemoglobin level measuring system can measure a first time associated with the first set of electrodes 112 as described above. At block 930, the glycated hemoglobin level measuring system can measure a second time associated with the second set of electrodes 114 as described above.

At block 940, the glycated hemoglobin level measuring system can calculate the channel passage time using the first and second times. At block 950, the glycated hemoglobin level measuring system can determine a glycated hemoglobin level based on the channel passage time and according to a predetermined pattern or relationship between the glycated hemoglobin level and the channel passage time.

In some embodiments, the glycated hemoglobin level measuring system can identify and analyze a subset of channel passage time data for determining the glycated hemoglobin level. For example, the glycated hemoglobin level measuring system can identify the data subset based on a total test duration. The glycated hemoglobin level measuring system can identify a test start time based on a first detected instance of the first time, such as representative of a first red blood cell entering the microchannel. Also, the glycated hemoglobin level measuring system can identify a test end time based on a last detected instance of the second time, such as representative of a last red blood cell exiting the microchannel. The glycated hemoglobin level measuring system can identify the subset of data that were captured during a specific portion or sub-duration between the test start time and the test end time. For example, the glycated hemoglobin level measuring system can identify the data subset as the impedance change events or the corresponding channel passage times during latter half of the test period or a targeted percentile range (e.g., between 60%-80% or other similar percentile range) of the total test duration. Accordingly, the glycated hemoglobin level measuring system can focus the analysis on more reliable readings, thereby removing environmental noise factors (e.g., capillary behavior, heat generated by the testing apparatus, or the like) and improving the measurement accuracy.

At block 960, the glycated hemoglobin level measuring system can adjust or personalize the calculated glycated hemoglobin level according to a reference glycated hemoglobin level that may be specific to the user. The reference glycated hemoglobin level may be measured at a medical facility. The adjustment of the glycated hemoglobin level may also be based on the size and/or type of the cells tested. This increases the measurement accuracy by adjusting for personal or individual characteristics.

In some embodiments, the glycated hemoglobin level measuring system can generate a distribution data of the calculated glycated hemoglobin levels (e.g., after adjusting and personalizing at block 960) for the analyzed data subset. For example, the glycated hemoglobin level measuring system can generate a distribution data similar to the distribution of the determined stiffness of red blood cells illustrated in FIGS. 8A and 8B. The generated distribution data can be used to determine and track over time a management status of the user's glycated hemoglobin level.

Figure 10:
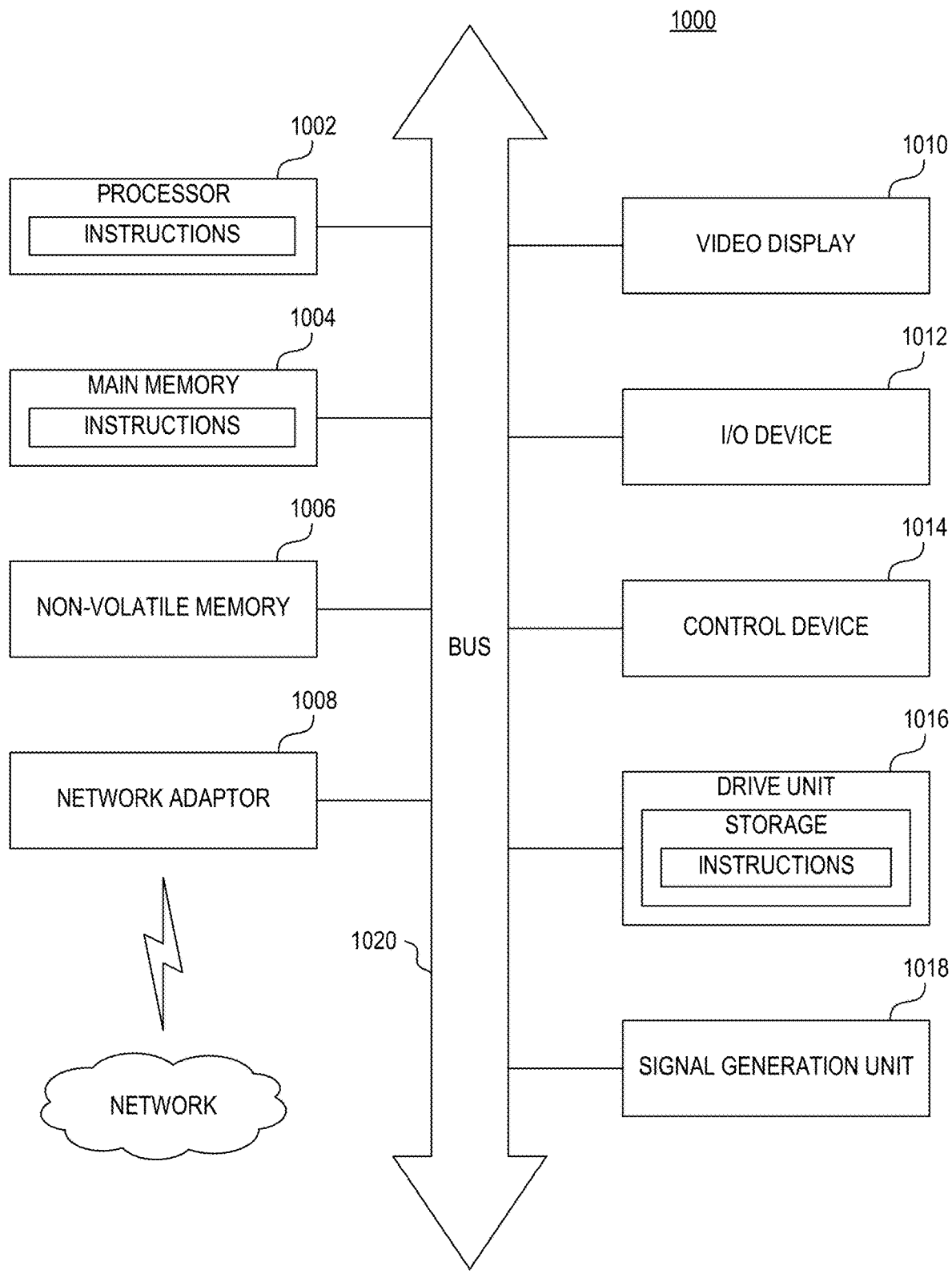
FIG. 10 is a block diagram illustrating an example of a processing system 1000 in which at least some operations described herein can be implemented.

FIG. 10 is a block diagram illustrating an example of a processing system 1000 in which at least some operations described herein can be implemented. For example, a computing device (e.g., the analysis apparatus 104, one or more client computing devices 120, or a combination thereof of FIG. 1) may be implemented using the processing system 1000.

The processing system 1000 may include one or more central processing units 1002 ("processors"), main memory 1004, non-volatile memory 1006, network adapters 1008 (e.g., network interfaces), video displays 1010, input/output devices 1012, control devices 1014 (e.g., keyboard and pointing devices), drive units 1016 including a storage medium, and/or signal generation devices 1018 that are communicatively connected to a bus 1020. The bus 1020 is illustrated as an abstraction that represents one or more physical buses and/or point-to-point connections that are connected by appropriate bridges, adapters, or controllers. The bus 1020, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1000 may operate in the capacity of a server or a client machine in a client-server network environment, or as a peer machine in a peer-to-peer network environment. The processing system 1000 may be an analysis circuit within a medical device, a server, a personal computer, a tablet computer, a personal digital assistant (PDA), a mobile phone, a gaming console, a gaming device, a music player, a wearable electronic device, a network-connected ("smart") device, a virtual/augmented reality system, or any other machine capable of executing a set of instructions (sequential or otherwise) that specify actions to be taken by the processing system 1000.

While the main memory 1004, the non-volatile memory 1006, and the storage medium (also called a "machine-readable medium") are shown to be a single medium, the term "machine-readable medium" and "storage medium" should be taken to include a single medium or multiple media (e.g., a centralized or distributed database, and/or associated caches and servers) that store one or more sets of instructions. The term "machine-readable medium" and "storage medium" shall also be taken to include any medium that is capable of storing, encoding, or carrying a set of instructions for execution by the processing system 1000.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions) set at various times in various memory and storage devices in a computing device. When read and executed by the one or more processors, the instruction(s) cause the processing system to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices, floppy and other removable disks, hard disk drives, optical disks (e.g., Compact Disk Read-Only Memory (CD ROMS), Digital Versatile Disks (DVDs)), and transmission-type media such as digital and analog communication links.

The network adapter 1008 enables the processing system to mediate data in a network with an entity that is external to the processing system through any communication protocol supported by the processing system and the external entity. The network adapter 1008 can include one or more of a network adaptor card, a wireless network interface card, a router, an access point, a wireless router, a switch, a multi-layer switch, a protocol converter, a gateway, a bridge, bridge router, a hub, a digital media receiver, and/or a repeater.

The network adapter 1008 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

As described above, in some embodiments, the degree of glycation may be measured using changes in the physical characteristics of red blood cells due to the glycation. In some embodiments, systems that use the disclosed technology (e.g., calculating mechanical properties, such as stiffness or hardness, of each individual red blood cell based on their microchannel passage time) may determine the degree of glycation more stably in response to external and human factors compared to equipment using biochemical techniques. In some embodiments, the glycated hemoglobin level measuring system can detect minute electrical changes that occur due to the passage of red blood cells using a circuit configuration and determine the degree of glycation of the red blood cells. In some embodiments, the glycated hemoglobin level measuring system can be used directly for clinical diagnosis by correcting an initial calculation of the glycated hemoglobin level using an individual user's reference value.

The systems can store one or more analyte management programs or protocols. In some embodiments, the analyte management program can indicate whether a measured analyte level is within a target or healthy range (e.g., HbA1c level of 4%-6% of total hemoglobin). The HbA1c level can indicate the subject-specific effectiveness of blood glucose management over a period of time, such as one or more months preceding the analysis. If the subject has a higher level (e.g., HbA1c level greater than 8% of total hemoglobin), the subject could be diabetic or pre-diabetic. The subject can take steps to lower the HbA1c level to acceptable target level (e.g., HbA1c level equal to or less than 5%, 6%, or 7% of total hemoglobin). The healthy range and target level can be inputted by the user, healthcare provider, or another source.

Furthermore, the glycated hemoglobin level measuring system can be implemented with a computer-readable storage medium or a similar device using, for example, software, hardware, or a combination thereof. In a hardware implementation, the glycated hemoglobin level measuring system can be implemented using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and electric units for performing other functions. In some embodiments, the glycated hemoglobin level measuring system may be implemented by a control module itself. In a software implementation, one or more aspects of the glycated hemoglobin level measuring system, such as the procedures and functions described above, may be implemented as separate software modules. Each of the software modules may perform one or more functions and operations described in the present specification. Software code may be implemented in software applications written in a suitable programming language. The software code may be stored in a memory module and may be executed by the control module.

The embodiments, features, systems, devices, materials, methods and techniques described herein may, in some embodiments, be similar to or include any one or more of the embodiments, features, systems, devices, materials, methods and techniques described in the following:

Korean Patent Application No.: 10-2021-0128520, filed Sep. 29, 2021, issued as Korean Patent No. 10-2439474;

International Application PCT/KR2021/018280, filed Dec. 3, 2021;

Korean Patent Application No. 10-2022-0031378, filed Mar. 14, 2022;

International Application PCT/KR2022/019905, filed Dec. 8, 2022; and

U.S. application Ser. No. 18/064,238 titled APPARATUS FOR MEASURING PROPERTIES OF PARTICLES IN A SOLUTION AND RELATED METHODS, filed on Dec. 9, 2022, and listing inventors: Ung-Hyeon Ko; Seung-Jin Kang; and Eun-Young Park.

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter.

The above description is merely illustrative of the technical idea of the present disclosure, and various modifications, changes, and substitutions may be made by those skilled in the art without departing from the essential features of the present disclosure. Accordingly, the embodiments described above and in the accompanying drawings are intended to describe the present technology without limiting the associated technical ideas. The scope of the present technology is not limited by any of the embodiments described above and the accompanying drawings.

It will be apparent to those having skill in the art that changes may be made to the details of the above-described embodiments without departing from the underlying principles of the present disclosure. In some cases, well known structures and functions have not been shown or described in detail to avoid unnecessarily obscuring the description of the embodiments of the present technology. Although steps of methods may be presented herein in a particular order, alternative embodiments may perform the steps in a different order. Similarly, certain aspects of the present technology disclosed in the context of particular embodiments can be combined or eliminated in other embodiments. Furthermore, while advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein, and the invention is not limited except as by the appended claims.

Throughout this disclosure, the singular terms "a," "an," and "the" include plural referents unless the context clearly indicates otherwise. Additionally, the term "comprising," "including," and "having" should be interpreted to mean including at least the recited feature(s) such that any greater number of the same feature and/or additional types of other features are not precluded.

Reference herein to "one embodiment," "an embodiment," "some embodiments" or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

Unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

The disclosure set forth above is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

We claim:

1. A glycated hemoglobin level measuring system, comprising:
    an analysis apparatus couplable to a sample testing apparatus including an inlet, an outlet, a microchannel connected between the inlet and the outlet, a first pair of electrodes contacting the microchannel, and a second pair of electrodes contacting the microchannel between the first pair and the outlet, the analysis apparatus including:
    a pump couplable to the inlet, the outlet, or both and configured to facilitate a transfer of blood sample with red blood cells suspended therein from the inlet to the outlet and through the microchannel that compresses the red blood cells;
    an electrical source couplable to the first and second pairs of electrodes and configured to communicate an input signal in parallel through (1) the first pair of electrodes and across a first detection region and (2) the second pair of electrodes and across a second detection region;
    a first sensor couplable to the first pair of electrodes and configured to detect a first change in impedance across the first detection region that represents a red blood cell reaching and passing through the first detection region;
    a second sensor couplable to the second pair of electrodes and configured to detect a second change in impedance across the second detection region that represents the red blood cell reaching and passing through the second detection region; and
    a logic configured to:
        detect a first time based on the first change in impedance;
        detect a second time based on the second change in impedance;
        calculate a time difference between the first and second times, wherein the time difference represents a travel period that is affected by a rigidity of the red blood cell; and
        determine a glycated hemoglobin level for the red blood cell based on the time difference,
            wherein the determined glycated hemoglobin level corresponds to the rigidity of the red blood cell.

2. The glycated hemoglobin level measuring system of claim 1, wherein the logic is configured to determine the glycated hemoglobin level based on:
    identifying a test start time representative of a first red blood cell crossing the first detection region;
    identifying a test end time representative of a last red blood cell crossing the second detection region;

identifying a subset of time differences for detected time events occurring within a targeted window between the test start time and the test end time; and determining the glycated hemoglobin level based the identified subset of time differences.

3. The glycated hemoglobin level measuring system of claim 2, wherein the targeted window is closer to the test end time than the test start time.

4. The glycated hemoglobin level measuring system of claim 2, wherein the logic is configured to:

determine a distribution of the subset of time differences or corresponding glycated hemoglobin levels; and determine a disease management status based on a shape of the distribution.

5. The glycated hemoglobin level measuring system of claim 4, wherein the logic is configured to:

determine the glycated hemoglobin level based on combining the glycated hemoglobin levels associated with the subset of time differences; and determine the disease management status as an improvement when (1) a maximum number of red blood cells having a level less than the determined glycated hemoglobin level is less than (2) a maximum number of red blood cells having a level greater than determined glycated hemoglobin level.

6. The glycated hemoglobin level measuring system of claim 1, wherein the logic is further configured to adjust the determined glycated hemoglobin level based on a reference glycated hemoglobin level that represents one or more predetermined personalized physiological conditions of a patient that provided the blood sample.

7. The glycated hemoglobin level measuring system of claim 1, wherein the first sensor includes:

a first resistor configured to connect in series with the first pair of electrodes; and a further resistor configured to connect (1) parallel to the first resistor and (2) in series with a third electrode on the sample testing apparatus that forms a following pair of electrodes with an overlapping electrode of the first pair of electrodes, wherein the first resistor and the further resistor are configured to form a Wheatstone bridge circuit when coupled to the first and the following pairs of electrodes, wherein a first component of the Wheatstone bridge includes the impedance across the first detection region in series with the first resistor, wherein a second component of the Wheatstone bridge includes the impedance across the second detection region in series with the further resistor, wherein the first sensor outputs an amplitude difference between the first and second components of the Wheatstone bridge.

8. The glycated hemoglobin level measuring system of claim 7, wherein:

the electrical source is configured to communicate the input signal to the overlapping electrode; and the first sensor is configured to identify a difference in signals entering the first resistor and the further resistor, wherein the signals entering the first resistor and the further resistor correspond to the input signal traversing through the first detection region and through a further detection region located between the overlapped electrode and the third electrode, and wherein the difference in the signals represent the red blood cell reaching and passing through the first detection region and then the further detection region.

9. The glycated hemoglobin level measuring system of claim 1, wherein the logic is configured to:

detect an error condition when the time difference is greater than a maximum threshold, wherein the error condition represents two red blood cells that entered the first detection region at different times simultaneously passing the second detection region; and omitting a test start time and a test end time associated with the time difference.

10. The glycated hemoglobin level measuring system of claim 1, wherein the input signal is a sinusoidal wave.

* * * * *